United States Patent [19]

de la Mettrie et al.

[11] Patent Number: 4,555,247

[45] Date of Patent: Nov. 26, 1985

[54] HAIR-DYEING COMPOSITIONS BASED ON NITRO DIRECT DYESTUFFS, AND A DYEING PROCESS USING THESE COMPOSITIONS

[75] Inventors: Roland de la Mettrie, Asnieres; Patrick Canivet, Paris, both of France

[73] Assignee: L'Oreal, Paris, France

[21] Appl. No.: 665,083

[22] Filed: Oct. 26, 1984

Related U.S. Application Data

[63] Continuation of Ser. No. 291,100, Aug. 7, 1981, abandoned.

[30] Foreign Application Priority Data

Aug. 8, 1980 [FR] France ............................... 80 17616
Jun. 16, 1981 [FR] France ............................... 81 11872

[51] Int. Cl.[4] ............................................... A61K 7/13
[52] U.S. Cl. ............................................ 8/405; 8/428
[58] Field of Search ..................................... 8/405, 428

[56] References Cited

U.S. PATENT DOCUMENTS 3,446,567  5/1969  Augustin et al. ..................... 8/410
3,733,175  5/1973  Alperin et al. ....................... 8/407
4,125,601 11/1978  Bugaut et al. ........................ 424/71

FOREIGN PATENT DOCUMENTS 1164824  9/1969  United Kingdom .
1403928  8/1975  United Kingdom .

OTHER PUBLICATIONS

Ames et al, "Dyes are Mutagenic; Identification of a Variety of Mutagenic Ingredients", *Proc. Nat. Acad. Sci.*, USA, vol. 72, No. 6, pp. 2, 423-2, 427 (Jun. 1975).

*Primary Examiner*—Albert T. Meyers
*Assistant Examiner*—John M. Kilcoyne
*Attorney, Agent, or Firm*—Fleit, Jacobson, Cohn & Price

[57] ABSTRACT

The dyeing compositions of the invention comprise at least one violet nitro dyestuff having a shade, on the Munsell scale, ranging from 7.5 P to 10 PB, and at least one yellow nitro dyestuff having a shade, on the Munsell scale, ranging from 10 Y to 2.5 Y, these violet and yellow dyestuffs being present in proportions such that their selectivity coefficients are substantially equal, the coefficients being from 3 to 8 when determined at a concentration of 0.1 to 0.6% by weight, the ratio by weight of the violet dyestuff to the yellow dyestuff being from 1:1 to 3:1.

17 Claims, No Drawings

HAIR-DYEING COMPOSITIONS BASED ON NITRO DIRECT DYESTUFFS, AND A DYEING PROCESS USING THESE COMPOSITIONS

This application is a continuation of application Ser. No. 291,100, filed Aug. 7, 1981, now abandoned.

The present invention relates to new dyeing compositions for the direct coloration of human hair, and especially of permed, natural or bleached hair.

Combinations of dyestuffs which make it possible to obtain a variety of shades are frequently used in hair dyeing. Thus, hair-dyeing compositions comprising violet nitro direct dyestuffs in combination with yellow nitro direct dyestuffs have already been used for obtaining natural colorations.

However, a difficulty arises when using such combinations of dyestuffs on hair of which the sensitivity to hair dyes differs from the root to the tip. This is the case, in particular, for hair of which the roots are natural and the tips have already been subjected to various treatments such as bleaching or perming. In this case, it is very difficult to obtain a good uniformity of coloration from the root to the tip of the hair, which will be stable with time, when using two or more dyestuffs in combination. In general, different colorations, depending on the degree of sensitisation of the hair, are found in such circumstances.

We have discovered, according to the present invention, that it is possible to obtain, on hair of which the degree of sensitisation varies from the root to the tip, a natural tint of which the shade is substantially the same from the root to the tip, by using a dyeing composition comprising at least one violet nitro dyestuff and at least one yellow nitro dyestuff, these dyestuffs being chosen from certain groups so that the violet dyestuff and the yellow dyestuff complement each other very well, possess a substantially equal selectivity and have substantially the same fastness to light, shampoos and perspiration.

The "selectivity" of a dyestuff means the difference in take-up of the dyestuff on the hair fibre, depending on whether the latter has been sensitised, and to what extent, by a treatment such as perming.

We have thus found that if dyestuffs of substantially equal selectivity and fastness are used in a dyeing composition, these dyestuffs have the same type of behaviour on hair which is of different sensitivity from the root to the tip and which has been subjected to the action of light, washing or perspiration, and that the dyeing thus obtained has a shade, the intensity of which can be weakened during a subsequent action of light etc., but the sheen of which remains the same from the root to the tip, regardless of the differences in sensitisation of the hair to the dye on passing from the root to the tip.

Thus, a violet dyestuff and a yellow dyestuff of substantially similar selectivity and fastness, which are both taken up, for example, more strongly on the tips of hair which has been subjected to a perming treatment, will, for example, be weakened in the same manner by light, washing or perspiration; consequently, the sheen of the shade will be preserved from the root to the tip of the hair because the two dyestuffs will have the same behaviour.

This desirable result is achieved, according to this invention, by using a dyeing composition for the direct coloration of human hair comprising at least one violet nitro dyestuff having a shade, on the Munsell scale, ranging from 7.5P to 10PB, and at least one yellow nitro dyestuff having a shade, on the Munsell scale, ranging from 10Y to 2.5Y, these dyestuffs being present in proportions such that their selectivity coefficients are substantially identical, the coefficients being from 3 to 8 when this is determined for a concentration of 0.1 to 0.6% by weight; the dyestuffs should generally have substantially the same fastness to light, shampoo and perspiration.

An additional condition for the violet and yellow dyestuffs to complement each other is that the ratio of the concentration of violet dyestuff by weight (sum of the violet dyestuffs) to the concentration of yellow dyestuff (sum of the yellow dyestuffs) is from 1:1 to 3:1.

"By substantially identical" selectivity coefficients is meant that the coefficients are equal ±1.

It is known that, according to Munsell's notation a colour is defined by the formula:

$$HV/C$$

in which the three parameters respectively denote the shade or "hue" (H), the intensity or "value" (V) and the purity or "chromaticity" (C), the oblique line being a simple convention.

The shade H can be expressed by a number followed by one or two letters characterising the colour, P meaning, for example, violet, B blue and Y yellow.

As regards Munsell's notation, reference may be made to the publication Official Digest, April 1964, page 375, FIG. 2 (ASTDM—1535—62), the disclosure of which is hereby incorporated by reference.

In view of the fact that the selectivity of a dyestuff varies with its concentration, it is more rational to define the selectivity coefficient of a given dyestuff at a given concentration. This coefficient thus makes it possible to compare different dyestuffs with one another.

The selectivity coefficient of a dyestuff can be determined in the following manner:

A swatch of unsensitised natural hair, that is to say a swatch which has not been subjected to a perming treatment, is dyed with the aid of a dyeing composition containing the dyestuff X at a concentration by weight $C_0$, under fixed dyeing conditions as regards the carrier, the pH and the temperature. An intensity $V_0$ is obtained.

A sensitised swatch, that is to say a swatch which has been subjected to a perming treatment, is dyed under the same dyeing conditions, but with dyeing compositions containing decreasing concentrations by weight $C_1, C_2 \ldots C_n$ of dyestuff X.

The concentration $C_n$ for which the intensity obtained on the sensitised swatch is the same as that obtained on the unsensitised swatch with the concentration $C_0$ of dyestuff X is sought.

The selectivity coefficient of the dyestuff X at the concentration $C_0$ in the given carrier is then defined as being the ratio:

$$S_{C_o} = C_0/C_n.$$

According to a preferred embodiment of the invention, we use, as violet dyestuffs, the N-substituted 2-nitro-p-phenylenediamines of the formula:

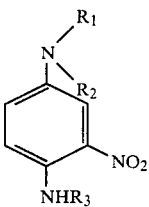

(I)

in which $R_1$ denotes the β-hydroxyethyl radical, $R_2$ denotes the β-hydroxyethyl or methyl radical and $R_3$ denotes the β-hydroxyethyl or methyl radical or additionally, the β-aminoethyl radical if $R_2$ denotes the β-hydroxyethyl radical, and, as yellow dyestuffs, the o- or p-nitroanilines of the formula:

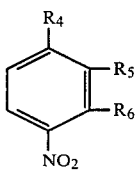

(II)

in which $R_4$ denotes hydrogen, $R_5$ denotes the isopropyl group and $R_6$ denotes the amino group; or alternatively $R_4$ denotes the β-hydroxyethoxy group, $R_5$ denotes hydrogen and $R_6$ denotes the methylamino or β-hydroxyethylamino group; or alternatively $R_4$ denotes the β,γ-dihydroxypropoxy group, $R_5$ denotes hydrogen and $R_6$ denotes the amino, methylamino or β-hydroxyethylamino group; or $R_4$ denotes the β-hydroxyethylamino group, $R_5$ denotes the methoxy group and $R_6$ denotes hydrogen; or alternatively $R_4$ denotes the methoxy group, $R_5$ denotes hydrogen and $R_6$ denotes the β-hydroxyethylamino, β-hydroxypropylamino or β,γ-dihydroxypropylamino group.

We have found not only that the above dyestuffs, used in combination in a dyeing composition, make it possible to obtain neutral and natural tints of which the sheen is preserved on passing from the unsensitised parts to the sensitised parts of the hair, and is only weakened by light, shampoos and perspiration, without being modified, but also that these dyestuffs possess the very valuable property of being non-mutagenic or only very weakly mutagenic.

In this specification, the non-mutagenic character of the dyestuffs is to be assessed in the Ames test on *Salmonella typhimurium*, with or without S 9 mix, with or without activation by Arochlor (prior treatment of the rats with Arochlor), and this is carried out on the five strains TA 1535, TA 1537, TA 100, TA 1538 and TA 98.

The Ames test is described, in particular, in the following publications: B. N. AMES, H. O. KAMMEN and E. YAMASAKI, "Dyes are mutagenic; Identification of a variety of mutagenic ingredients", Proc. Nat. Acad. Sci, USA, Volume 72, No. 6, pages 2,423–2,427 (June 1975); and B. N. AMES, J. McCANN and E. YAMASAKI, "Methods for detecting carcinogens and mutagens with Salmonella mammalian microsome mutagenicity test", Mutation Res., 31 (1975), pages 347–364.

As used herein, the expression "very weakly mutagenic" means that the composition has less than twice the number of mutants as the control. Such a test, described by Ames et al, loc cit, is considered by the authors to be negative.

According to another characteristic of the present invention, the sum of the concentrations of the violet dyestuffs and the yellow dyestuffs contained in the dyeing compositions of the invention is preferably from 0.04% to 2.5% by weight.

Apart from the violet dyestuffs and the yellow dyestuffs indicated above, the dyeing compositions according to the invention can contain, as auxiliary dyestuffs, other nitro dyestuffss which make it possible to obtain shades containing various proportions of red and various proportions of gold or copper and having a variety of attractive and natural sheens.

These dyestuffs should always have a lower selectivity than that of the violet and yellow dyestuffs of the formulae (I) and (II).

Particularly suitable dyestuffs for use in combination with the abovementioned violet and yellow dyestuffs are the 3-nitro-aminophenols of the formula:

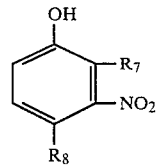

(III)

in which $R_7$ denotes hydrogen and $R_8$ denotes an amino or β-hydroxyethylamino group, or, alternatively, $R_7$ denotes the amino group and $R_8$ denotes hydrogen.

Other particularly suitable auxiliary dyestuffs are orange to yellow nitro-aminobenzenes having the formula:

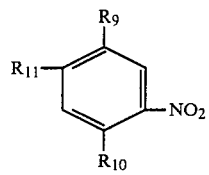

(IV)

in which $R_9$ denotes the hydroxyl group, $R_{10}$ denotes hydrogen and $R_{11}$ denotes the N-(β-hydroxyethyl)-amino group, or alternatively $R_9$ denotes the β-hydroxyethoxy or β,γ-dihydroxypropoxy group, $R_{10}$ denotes the N-(β-hydroxyethyl)-amino group and $R_{11}$ denotes hydrogen.

We have found furthermore that the dyestuffs of the abovementioned formula (III) or (IV) have the advantage of being non-mutagenic or very weakly mutagenic in the Ames test.

The dyeing compositions according to the invention generally contain from 0.001 to 2.5% by weight and preferably from 0.005 to 1.5% by weight of one or more dyestuffs of the above formulae (III) and/or (IV).

Apart from the nitro direct dyestuffs defined above, the dyeing compositions according to the invention can comprise, in an aqueous vehicle, for example, a solvent, such as an alcohol, such as ethyl alcohol, isopropyl alcohol or benzyl alcohol, or a glycol or glycol ether, such as butylglycol, ethylene glycol, propylene glycol, ethylene glycol monoethyl ether, carbitol or butylcarbitol, generally in concentrations of 0.5 to 20% by weight and preferably 2 to 10% by weight.

They can also contain anionic, cationic, amphoteric or non-ionic surface-active agents or a mixture thereof, in concentrations which are generally 0.05 to 50% by weight and preferably 0.5 to 10% by weight.

Amongst the anionic surface-active agents used singly or as a mixture, the following examples may be mentioned: the alkali metal salts, the magnesium salts, the ammonium salts, the amine salts or the alkanolamine salts of the following compounds:

alkyl-sulphates, alkyl-ether-sulphates and oxyethyleneated or non-oxyethyleneated alkylamide-sulphates, alkylsulphonates, alkylamidesulphonates and alpha-olefinesulphonates, and alkyl-sulphoacetates, the alkyl radicals of these compounds having a linear $C_{12}$ to $C_{18}$ chain, and fatty acids such as lauric, myristic, oleic, ricinoleic, palmitic and stearic acids, acids derived from copra oil or from hydrogenated copra oil, and carboxylic acids of polyglycol ethers.

Amongst the cationic surface-active agents which can be used singly or as a mixture, the following may be mentioned in particular:

fatty amine salts, quaternary ammonium salts such as alkyldimethylbenzylammonium, alkyltrimethylammonium, alkyldimethylhydroxyethylammonium and dimethyldistearylammonium chlorides and bromides, alkylpyridinium salts and imidazoline derivatives.

Compounds of cationic character, such as amine oxides, may also be mentioned.

Amongst the amphoteric surface-active agents which can be used, the following may be mentioned in particular:

alkylamino mono- and di-propionates, betains such as alkylbetains, N-alkyl-sulphobetains and N-alkylaminobetains, the alkyl radical containing from 1 to 22 carbon atoms, and cycloimidinium compounds such as alkylimidazolines.

The following may be mentioned amongst the non-ionic surface-active agents which can, if desired, be used as a mixture with the abovementioned anionics and/or cationics:

the condensation products of a monoalcohol, a α-diol, an alkylphenol or an amide with glycidol, for example the compounds of the formula R—CHOH—CH$_2$—O—(CH$_2$—CHOH—CH$_2$—O$)_{\overline{n_2}}$H, in which R denotes an aliphatic, cycloaliphatic or arylaliphatic radical having from 7 to 21 carbon atoms, and mixtures thereof, it being possible for the aliphatic chains to contain ether, thioether and hydroxymethylene groups, and $n_2$ being an integer such that $1 \leq n_2 \leq 10$, and the compounds of the formula RO—(C$_2$H$_3$O(CH$_2$OH)$)_{\overline{n_3}}$H, in which R denotes an alkyl, alkenyl or alkylaryl radical having 8 to 22 carbon atoms and $1 \leq n_3 \leq 10$, polyoxyethyleneated or polyglycerolated fatty alcohols, fatty alkylphenols or fatty acids having a linear $C_8$ to $C_{18}$ fatty chain, condensation products of ethylene oxide and propylene oxide with fatty alcohols, polyoxyethyleneated fatty amides and polyoxyethyleneated fatty amines.

The dyeing compositions according to the invention can also contain fatty amides such as the mono- and di-ethanolamides of acids derived from copra, of lauric acid or of oleic acid, suitably at concentrations of 0.05 to 10% by weight.

The dyeing compositions according to the invention can also contain thickeners such as sodium alginate, gum arabic, or cellulose derivatives such as methylcellulose, hydroxymethylcellulose, hydroxyethylcellulose and hydroxypropylcellulose, suitably in concentrations of 0.5 to 15% by weight.

Apart from the abovementioned ingredients, they can contain adjuvants such as perfumes, preservatives and sequestering agents.

The pH of the dyeing compositions according to the invention is generally from 6 to 11, but is preferably from 8 to 10.

It can be adjusted with alkaline agents such as monoethanolamine, diethanolamine, triethanolamine, ammonia, ammonium, potassium or sodium carbonate or sodium hydroxide, or with acidifying agents such as phosphoric, hydrochloric, tartaric, acetic, lactic or citric acids.

The dyeing compositions according to the invention can be presented in various customary forms such as thickened liquids, foaming liquids, and aerosol foams.

They can be applied to natural hair or permed natural hair or to permed or unpermed, strongly or lightly bleached hair.

The present invention thus also provides a process for dyeing human hair by direct coloration.

According to a preferred embodiment of the invention, the hair is subjected to a lightening treatment, either with the aid of an ammoniacal solution of hydrogen peroxide or a solution of hydrogen peroxide containing an alkaline agent such as an aliphatic or hydroxyaliphatic amine, or with the aid of an ammoniacal solution of an alkali metal peroxide or per-salt, such as sodium peroxide, potassium peroxide, sodium perborate or sodium percarbonate, of urea peroxide, or of an addition compound of hydrogen peroxide and an organic compound, such as melanin perhydrate.

This lightening solution is applied to the head of hair and left for, say, 5 to 30 minutes, depending on the lightening desired, after which the hair is rinsed with water and the dyeing composition according to the invention is applied and left for, say, 15 to 30 minutes at ambient temperature; the hair is then rinsed and dried. According to another variant, the lightening solution and the dyeing solution according to the invention are applied to the head of hair simultaneously. After an interval of, say, 15 to 30 minutes, the hair is rinsed and dried.

The dyeing compositions according to the invention make it possible to obtain, on permed hair, a uniform coloration in a shade of which the sheen is preserved from the root to the tip of the hair, without being modified by light, shampoos or perspiration.

The present·invention is further illustrated in the following Examples.

PREPARATION EXAMPLE 1

Preparation of
3-nitro-4-[N-(β-hydroxyethyl)-amino]-phenoxyethanol

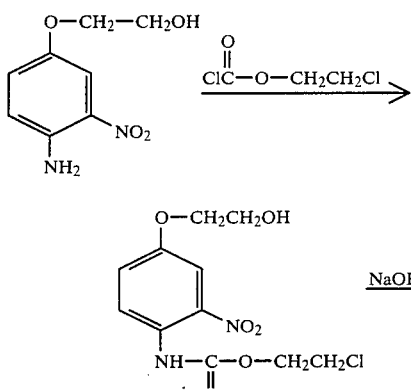

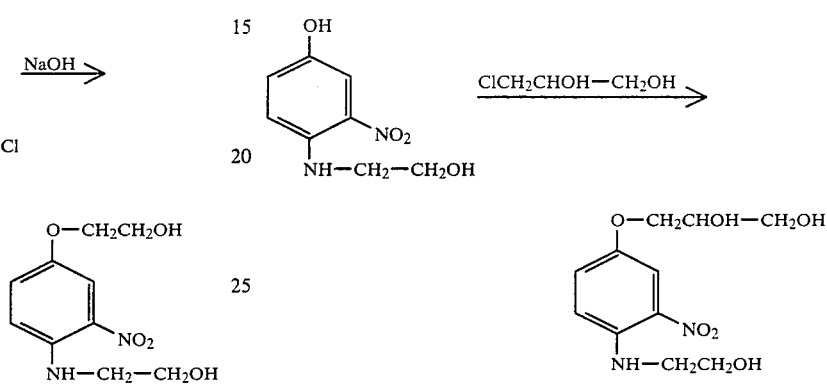

1ST STEP

Preparation of β-chloroethyl
2-nitro-4-(β-hydroxyethoxy)-phenylcarbamate

The starting material used is the 3-nitro-4-aminophenoxyethanol described in Example 1 of French Pat. No. 2,290,186.

4 mols (792 g) of 3-nitro-4-aminophenoxyethanol are dissolved in 1,600 ml of dioxane. 2.4 mols (240 g) of calcium carbonate are added. The temperature is raised to about 90° C. and 4.8 mols (686 g) of β-chloroethyl chloroformate are then introduced gradually, whilst stirring. When the addition has ended, heating is maintained for 30 minutes at 90° C. The reaction medium is filtered hot. The cooled filtrate is diluted with petroleum ether to precipitate the desired product, which, after recrystallisation from dioxane and drying in vacuo, melts at 119° C.

2ND STEP

Preparation of
3-nitro-4-[N-(β-hydroxyethyl)-amino]-phenoxyethanol 0.1 mol (30.45 g) of β-chloroethyl 2-nitro-4-(β-hydroxyethoxy)-phenylcarbamate is introduced into 62 ml of water. 10 ml of 10N sodium carbonate solution are added gradually in the course of a few minutes, whilst stirring. The temperature rises to about 60° C. The temperature of the reaction medium is then raised to 70° C. and 22 ml of 10N sodium carbonate solution are then added, whilst stirring. Stirring is continued for 15 minutes at 70° C. After cooling, the desired product is filtered off; after washing with water, drying and recrystallisation from methanol, it melts at 82° C.

| Analysis | Calculated for $C_{10}H_{14}O_5N_2$ | Found |
|---|---|---|
| C % | 49.58 | 49.72 |
| H % | 5.33 | 5.82 |
| N % | 11.57 | 11.62 |
| O % | 33.03 | 33.00 |

PREPARATION EXAMPLE 2

Preparation of
3-nitro-4-[N-(β-hydroxyethyl)-amino]-phenyl
β,γ-dihydroxypropyl ether 0.2 mol (39.6 g) of 3-nitro-4-[N-(β-hydroxyethyl)-amino]-phenol is dissolved in 125 ml of 2N sodium carbonate solution. 0.25 mol (27.5 g) of 1-chloropropane-2,3-diol is added to this solution, heated beforehand to about 90° C. Heating is maintained for a further 2 hours. After cooling, the reaction medium is extracted with ethyl acetate. After the solvent has been evaporated off to dryness, 29 g of the desired product are obtained in the form of orange crystals.

After recrystallisation from isopropanol and drying in vacuo, the product melts at 102° C.

| Analysis | Calculated for $C_{11}H_{16}N_2O_6$ | Found |
|---|---|---|
| C % | 48.52 | 48.53 |
| H % | 5.92 | 5.88 |
| N % | 10.29 | 10.29 |

EXAMPLE 3

A lightening solution is prepared by mixing 30 g of hydrogen peroxide of 20 volumes strength with 10 g of an aqueous solution containing 3.5% of ammonia and 4% of hydroxyethylcellulose. This solution is applied to hair which has been subjected to a perming treatment some time previously and which will be referred to as "hair with permed tips." After an interval of 15 minutes, the hair is rinsed with water.

The following dyeing composition is prepared:

| | |
|---|---|
| $N^1$—Methyl-$N^4,N^4$—bis-(β-hydroxyethyl)-2-nitro-p-phenylenediamine | 2.5 g |
| 4-Nitro-3-(methylamino)-phenoxyethanol | 1.1 g |
| 3-Nitro-4-[N—(β-hydroxyethyl)-amino]-phenoxyethanol | 0.15 g |
| 3-Nitro-4-(β-hydroxyethylamino)-phenol | 0.18 g |
| Laurylamide | 15 g |
| Lauric acid | 10 g |
| Butylglycol | 60 g |

| | |
|---|---|
| Hydroxyethylcellulose | 50 g |
| Monoethanolamine q.s.p. | pH 9 |
| Water q.s.p. | 1,000 g |

This composition is applied to hair with permed tips, which has been subjected to the above lightening pre-treatment. After an interval of 30 minutes at ambient temperature and rinsing with water, this composition imparts a pearlescent golden blond coloration. The sheen of the shade is preserved from the root to the tip, without being modified by light or perspiration.

EXAMPLE 4

The lightening solution of Example 3 and the following dyeing composition:

| | |
|---|---|
| $N^1$—Methyl-$N^4$,$N^4$—bis-($\beta$-hydroxyethyl)-2-nitro-p-phenylenediamine | 2.5 g |
| 4-Nitro-3-(methylamino)-phenoxyethanol | 1 g |
| 3-Nitro-2-aminophenol | 1.75 g |
| 3-Nitro-4-($\beta$-hydroxyethylamino)-phenol | 5 g |
| 3-Nitro-6-[N—($\beta$-hydroxyethyl)-amino]-phenol | 1.5 g |
| Laurylamide | 15 g |
| Lauric acid | 10 g |
| Butylglycol | 60 g |
| Hydroxyethylcellulose | 50 g |
| Monoethanolamine q.s.p. | pH 9 |
| Water q.s.p. | 1,000 g | are applied simultaneously to hair with permed tips.

After an interval of 30 minutes at ambient temperature, followed by rinsing, this composition imparts an intense coppery-red coloration to the hair. It is noted that this coloration is more intense on the tips, but that the sheen of the shade is preserved from the root to the tip of the hair. It is weakened by light or perspiration, without being modified.

EXAMPLE 5

The following dyeing composition is prepared:

| | |
|---|---|
| $N^1$—Methyl-$N^4N^4$—bis-($\beta$-hydroxyethyl)-2-nitro-p-phenylenediamine | 2.5 g |
| 4-Nitro-3-(methylamino)-phenoxyethanol | 1 g |
| 3-Nitro-4-[N—($\beta$-hydroxyethyl)-amino]-phenyl $\beta,\gamma$-dihydroxypropyl ether | 2 g |
| Laurylamide | 15 g |
| Lauric acid | 10 g |
| Butylglycol | 60 g |
| Hydroxyethylcellulose | 50 g |
| Monoethanolamine q.s.p. | pH 9 |
| Water q.s.p. | 1,000 g |

When applied for 30 minutes to natural hair with permed tips, this composition imparts to the hair, after rinsing and drying, a coppery mahogany light blond coloration.

The same observations can be made as in the preceding example as regards the sheen of the shade.

EXAMPLE 6

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1,N^4,N^4$—Tri-($\beta$-hydroxyethyl)-2-nitro-p-phenylenediamine | 7.0 g |
| 2-Isopropyl-o-nitroaniline | 3.8 g |
| Monoethanolamine q.s.p. | pH 9 |
| Water q.s.p. | 1,000 g |

This composition is applied to hair which has been subjected to the lightening pre-treatment of Example 3. After an interval of 30 minutes at ambient temperature, the hair is rinsed and dried. This solution imparts a very uniform, natural coloration. It is noted that this coloration is more intense on the permed parts, that is to say on the tips, but that the sheen of the shade is preserved from the root to the tip of the hair. It is weakened by light or perspiration, without being modified.

EXAMPLE 7

The lightening solution of Example 1 and the following dyeing composition:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 0.5 g |
| 2-Isopropyl-o-nitroaniline | 0.3 g |
| Monoethanolamine q.s.p. | pH 9 |
| Water q.s.p. | 1,000 g | are applied simultaneously to hair with permed tips.

After an interval of 20 minutes at ambient temperature and rinsing with water, this composition imparts a very uniform, natural coloration. It is found that substantially the same results are obtained as in Example 1.

EXAMPLE 8

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 2.0 g |
| 4-Nitro-3-(methylamino)-phenoxyethanol | 0.8 g |
| Monoethanolamine q.s.p. | pH 9 |
| Water q.s.p. | 1,000 g |

This composition is applied to natural hair which has been permed a few weeks previously. After an interval of 15 minutes at ambient temperature, the hair is rinsed. This solution imparts a uniform natural coloration; in other respects, the same results are observed as previously.

EXAMPLE 9

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 1.4 g |
| 2-Isopropyl-o-nitroaniline | 0.9 g |
| 3-Nitro-4-aminophenol | 0.15 g |
| Monoethanolamine q.s.p. | pH 9 |

| Water q.s.p. | 1,000 g |

The above composition is applied to hair with permed tips, which has been subjected to the lightening pre-treatment of Example 1. After an interval of 15 minutes at ambient temperature, the hair is rinsed and dried. This solution imparts a very uniform, natural blond coloration. The same results are noted as in Example 1.

EXAMPLE 10

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4,N^4$—bis-($\beta$-hydroxyethyl)-2-nitro-p-phenylenediamine | 4.6 g |
| 3-Nitro-4-aminophenol | 0.3 g |
| 3-Nitro-4-($\beta$-hydroxyethylamino)-phenol | 0.36 g |
| 4-Nitro-3-(methylamino)-phenoxyethanol | 2.3 g |
| Monoethanolamine q.s.p. | pH 9 |
| Water q.s.p. | 1,000 g |

This composition is applied to natural hair with permed tips. After an interval of 20 minutes at ambient temperature and rinsing with water, this solution imparts a very uniform, golden deep blond coloration. The sheen of the shade is also preserved from the root to the tip of the hair.

EXAMPLE 11

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4,N^4$—bis-($\beta$-hydroxyethyl)-2-nitro-p-phenylenediamine | 4.0 g |
| 2-Isopropyl-o-nitroaniline | 3.5 g |
| 3-Nitro-4-($\beta$-hydroxyethylamino)-phenol | 3.0 g |
| Monoethanolamine q.s.p. | pH 9 |
| Water q.s.p. | 1,000 g |

This composition is applied to hair with permed tips, which has been subjected to the lightening pretreatment of Example 1. After an interval of 20 minutes at ambient temperature and rinsing with water, this solution imparts a very uniform, iridescent red, deep blond coloration. In other respects, the results are identical to those obtained above.

EXAMPLE 12

The lightening solution of Example 1 and the following dyeing composition:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4,N^4$—bis-($\beta$-hydroxyethyl)-2-nitro-p-phenylenediamine | 1.1 g |
| 4-Nitro-3-(methylamino)-phenoxyethanol | 0.5 g |
| 3-Nitro-4-aminophenol | 0.06 g |
| Monoethanolamine q.s.p. | pH 9 |
| Water q.s.p. | 1,000 g | are applied simultaneously to hair with permed tips.

After an interval of 25 minutes at ambient temperature and rinsing with water, this solution imparts a very uniform, natural light blond coloration. In other respects, the same results are noted as previously.

EXAMPLE 13

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4,N^4$—bis-($\beta$-hydroxyethyl)-2-nitro-p-phenylenediamine | 2.6 g |
| 2-Isopropyl-o-nitroaniline | 2.6 g |
| 3-Nitro-4-aminophenol | 0.25 g |
| 3-Nitro-4-($\beta$-hydroxyethylamino)-phenol | 0.2 g |
| Monoethanolamine q.s.p. | pH 9 |
| Water q.s.p. | 1,000 g |

This composition is applied to natural hair with permed tips; after an interval of 30 minutes at ambient temperature and rinsing with water, this solution imparts a very uniform, golden blond coloration. In other respects, the results are identical to those obtained previously.

EXAMPLE 14

The following dyeing composition is prepared:

| | |
|---|---|
| Laurylamide | 15 g |
| Lauric acid | 10 g |
| Butylglycol | 60 g |
| Hydroxyethylcellulose | 50 g |
| 3-Nitro-4-($\beta$-hydroxyethylamino)-phenol | 3.5 g |
| 4-Nitro-3-(methylamino)-phenoxyethanol | 2.5 g |
| $N^1,N^4,N^4$—Tri-($\beta$-hydroxyethyl)-2-nitro-p-phenylenediamine | 4.5 g |
| Monoethanolamine q.s.p. | pH 9 |
| Water q.s.p. | 1,000 g |

This composition is applied to hair with permed tips, which has been subjected to the lightening pretreatment of Example 1. After an interval of 30 minutes at ambient temperature and rinsing with water, this solution imparts a very uniform, mahogany chestnut coloration. In other respects, the results noted are identical to those obtained previously.

EXAMPLE 15

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1,N^4,N^4$—Tri-($\beta$-hydroxyethyl)-2-nitro-p-phenylenediamine | 4 g |
| 2-Isopropyl-o-nitroaniline | 4 g |
| 3-Nitro-4-($\beta$-hydroxyethylamino)-phenol | 4 g |
| Monoethanolamine q.s.p. | pH 9 |
| Water q.s.p. | 1,000 g |

This composition is applied to hair with permed tips, which has been subjected to the lightening pretreatment of Example 1. After an interval of 25 minutes at ambient temperature, the hair is rinsed and dried. This solution imparts a very uniform, mahogany chestnut coloration. In other respects, the results noted are substantially identical to those obtained previously.

EXAMPLE 16

The following dyeing composition is prepared:

| | |
|---|---|
| Laurylamide | 15 g |
| Lauric acid | 10 g |
| Butylglycol | 60 g |
| Hydroxyethylcellulose | 50 g |
| 4-Nitro-3-(methylamino)-phenoxyethanol | 0.85 g |
| $N^1,N^4,N^4$—Tri-($\beta$-hydroxyethyl)-2-nitro-p-phenylenediamine | 2.5 g |
| 3-Nitro-4-aminophenol | 0.1 g |
| Monoethanolamine q.s.p. | pH 9 |
| Water q.s.p. | 1,000 g |

This composition is applied to lightly bleached hair with permed tips, according to Example 1. After an interval of 30 minutes at ambient temperature and rinsing with water, this solution imparts a very uniform, light blond coloration. The sheen of the shade is preserved from the root to the tip. It is weakened by light or perspiration, without being modified.

EXAMPLE 17

The lightening solution of Example 1 and the following dyeing composition:

| | |
|---|---|
| Laurylamide | 15 g |
| Lauric acid | 10 g |
| Butylglycol | 60 g |
| Hydroxyethylcellulose | 50 g |
| $N^1,N^4,N^4$—Tri-($\beta$-hydroxyethyl)-2-nitro-p-phenylenediamine | 1.05 g |
| 2-Isopropyl-o-nitroaniline | 0.55 g |
| 3-Nitro-4-aminophenol | 0.10 g |
| 3-Nitro-4-($\beta$-hydroxyethylamino)-phenol | 0.05 g |
| Monoethanolamine q.s.p. | pH 9 |
| Water q.s.p. | 1,000 g | are applied simultaneously to hair which has been permed a few weeks previously.

After an interval of 25 minutes at ambient temperature and rinsing with water, this solution imparts a very uniform, golden light blond coloration. The same results are noted as previously.

EXAMPLE 18

The following dyeing composition is prepared:

| | |
|---|---|
| Laurylamide | 15 g |
| Lauric acid | 10 g |
| Butylglycol | 60 g |
| Hydroxyethylcellulose | 50 g |
| 2-Isopropyl-o-nitroaniline | 0.65 g |
| 3-Nitro-4-aminophenol | 0.10 g |
| $N^1,N^4,N^4$—Tri-($\beta$-hydroxyethyl)-2-nitro-p-phenylenediamine | 1.15 g |
| Monoethanolamine q.s.p. | pH 9 |
| Water q.s.p. | 1,000 g |

The composition is applied to lightly bleached hair with permed tips, according to Example 1. After an interval of 30 minutes at ambient temperature and rinsing with water, this solution imparts a very uniform, light chestnut coloration. The same results are noted as previously.

EXAMPLE 19

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4,N^4$—bis-($\beta$-hydroxyethyl)-2-nitro-p-phenylenediamine | 1.4 g |
| 2-Isopropyl-o-nitroaniline | 1.0 g |
| 3-Nitro-4-aminophenol | 0.12 g |
| 4-Nitro-3-(methylamino)-phenoxyethanol | 0.6 g |
| $N^1,N^4,N^4$—Tri-($\beta$-hydroxyethyl)-2-nitro-p-phenylenediamine | 1.45 g |
| Monoethanolamine q.s.p. | pH 9 |
| Water q.s.p. | 1,000 g |

The composition is applied to hair with permed tips, which has been subjected to the lightening pretreatment of Example 1. After an interval of 20 minutes at ambient temperature and rinsing with water, this solution imparts a very uniform, deep blond coloration. The same results are observed as previously.

EXAMPLE 20

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—($\beta$-Hydroxyethyl)-$N^4$—methyl-$N^4$—($\beta$-hydroxyethyl)-2-nitro-p-phenylenediamine | 3 g |
| 4-Nitro-3-(methylamino)-phenoxyethanol | 1.3 g |
| Monoethanolamine q.s.p. | pH 9 |
| Water q.s.p. | 1,000 g |

This composition is applied to hair with permed tips, which has been subjected to the lightening pretreatment of Example 1.

After an interval of 15 minutes at ambient temperature and rinsing with water, a very uniform, natural coloration is obtained. It is noted that this coloration is more intense on the permed parts, but that the sheen of the shade is preserved. It is weakened by light or perspiration, without being modified.

EXAMPLE 21

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$—methyl-$N^4$—($\beta$-hydroxyethyl)-2-nitro-p-phenylenediamine | 3 g |
| 4-Nitro-3-(methylamino)-phenoxyethanol | 1.5 g |
| Monoethanolamine q.s.p. | pH 9 |
| Water q.s.p. | 1,000 g |

This composition is applied to natural hair with permed tips. After an interval of 20 minutes at ambient temperature and rinsing with water, a very uniform, natural coloration is obtained. In other respects, the same results are noted as in the previous example.

EXAMPLE 22

The lightening solution of Example 1 and the following dyeing composition:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$—methyl-$N^4$—($\beta$-hydroxyethyl)-2-nitro-p-phenylenediamine | 3 g |
| 4-Nitro-2-methoxy-$\beta$-hydroxyethylaniline | 0.7 g |
| 3-Methylamino-4-nitrophenyl $\beta,\gamma$-dihydroxypropyl ether | 0.5 g |
| Monoethanolamine q.s.p. | pH 9 |
| Water q.s.p. | 1,000 g | are applied simultaneously to hair which has been permed a few weeks previously.

After an interval of 20 minutes and rinsing with water, a very uniform, natural coloration is obtained; in other respects, the results noted are similar to those obtained previously.

EXAMPLE 23

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—($\beta$-Aminoethyl)-$N^4$.$N^4$—bis-($\beta$-hydroxyethyl)-2-nitro-p-phenylenediamine | 2 g |
| 2-Isopropyl-o-nitroaniline | 1.6 g |
| Monoethanolamine q.s.p. | pH 9 |
| Water q.s.p. | 1,000 g |

This composition is applied to natural hair with permed tips. After an interval of 30 minutes at ambient temperature and rinsing with water, a very uniform, natural coloration is obtained. The sheen of the shade is preserved from the root to the tip. It is weakened by light or perspiration, without being modified.

EXAMPLE 24

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 2 g |
| 3-Methylamino-4-nitrophenyl $\beta,\gamma$-dihydroxypropyl ether | 1.1 g |
| Monoethanolamine q.s.p. | pH 9 |
| Water q.s.p. | 1,000 g |

This composition is applied to hair with permed tips, which has been subjected to the lightening pretreatment of Example 1. After an interval of 25 minutes and rinsing with water, a very uniform, natural coloration is obtained. In other respects, the same results are noted as previously.

EXAMPLE 25

The following dyeing composition is prepared:

| | |
|---|---|
| Laurylamide | 15 g |
| Lauric acid | 10 g |
| Butylglycol | 60 g |
| Hydroxyethylcellulose | 50 g |
| 4-Nitro-3-($\beta$-hydroxyethylamino)-phenoxyethanol | 1.8 g |
| $N^1$—Methyl-$N^4$,$N^4$—bis-($\beta$-hydroxyethyl)-2-nitro-p-phenylenediamine | 2.8 g |
| 3-Nitro-4-aminophenol | 0.15 g |
| Monoethanolamine q.s.p. | pH 9 |
| Water q.s.p. | 1,000 g |

This composition is applied to previously bleached hair with permed tips, according to Example 1.

After an interval of 20 minutes and rinsing with water, a very uniform, natural blond coloration is obtained. The sheen of the shade is preserved from the root to the tip, without being modified by light or perspiration.

EXAMPLE 26

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 2.6 g |
| 3-($\beta$-Hydroxyethylamino)-4-nitrophenyl $\beta,\gamma$-dihydroxypropyl ether | 2.1 g |
| Monoethanolamine q.s.p. | pH 9 |
| Water q.s.p. | 1,000 g |

This composition is applied to hair with permed tips, which has been subjected to the lightening pretreatment of Example 1. After an interval of 20 minutes and rinsing with water, a very uniform, natural coloration is obtained. In other respects, the same results are noted as previously.

EXAMPLE 27

The following dyeing composition is prepared:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 3 g |
| 3-($\beta$-Hydroxypropylamino)-4-nitroanisole | 1.8 g |
| Monoethanolamine q.s.p. | pH 9 |
| Water q.s.p. | 1,000 g |

This composition is applied to natural hair with permed tips. After an interval of 25 minutes and rinsing with water, a very uniform, natural coloration is observed. The sheen of the shade is preserved from the root to the tip, without being modified by light or perspiration.

EXAMPLE 28

The lightening solution of Example 1 and the following dyeing composition:

| | |
|---|---|
| Laurylamide | 15 g |
| Lauric acid | 10 g |
| Butylglycol | 60 g |
| Hydroxyethylcellulose | 50 g |
| $N^1$—Methyl-$N^4$,$N^4$—bis-($\beta$-hydroxyethyl)-2-nitro-p-phenylenediamine | 3 g |

-continued

| 3-(β,γ-Dihydroxypropylamino)-4-nitroanisole | 2 g |
|---|---|
| Monoethanolamine q.s.p. | pH 9 |
| Water q.s.p. | 1,000 g | are applied simultaneously to hair which has been permed a few weeks previously.

After an interval of 15 minutes and rinsing with water, a very uniform, natural coloration is obtained. In other respects, the same results are noted as previously.

EXAMPLE 29

The following dyeing composition is prepared:

| Laurylamide | 15 g |
|---|---|
| Lauric acid | 10 g |
| Butylglycol | 60 g |
| Hydroxyethylcellulose | 50 g |
| $N^1$—Methyl-$N^4,N^4$—bis-(β-hydroxyethyl)-2-nitro-p-phenylenediamine | 3 g |
| 3-(β-Hydroxyethylamino)-4-nitroanisole | 1.3 g |
| Monoethanolamine q.s.p. | pH 9 |
| Water q.s.p. | 1,000 g |

This composition is applied to hair with permed tips, which has been subjected to the lightening pretreatment of Example 1. After an interval of 20 minutes and rinsing with water, a very uniform, natural coloration is obtained. It is noted that this coloration is more intense on the permed parts, but that the sheen of the shade is preserved from the root to the tip. It is weakened by light or perspiration, without being modified.

EXAMPLE 30

The following dyeing composition is prepared:

| $N^1$—Methyl-$N^4,N^4$—bis-(β-hydroxyethyl)-2-nitro-p-phenylenediamine | 2 g |
|---|---|
| 3-Amino-4-nitrophenyl β,γ-dihydroxypropyl ether | 1.7 g |
| 3-Nitro-4-aminophenol | 0.15 g |
| Laurylamide | 15 g |
| Lauric acid | 10 g |
| Butylglycol | 60 g |
| Hydroxyethylcellulose | 50 g |
| Monoethanolamine q.s.p. | pH 9 |
| Water q.s.p. | 1,000 g |

This composition is applied to natural grey hair with permed tips. After an interval of 25 minutes at ambient temperature and rinsing with water, this composition imparts a natural blond coloration. This sheen of the shade is preserved from the root to the tip, without being modified by light or perspiration.

We claim:

1. A composition having less than twice the number of mutants as the control, as tested by the Ames test, which is suitable for the direct coloration of human hair, said composition comprising at least one violet nitro dyestuff having a shade, on the Munsell scale, from 7.5 P to 10 PB, and at least one yellow nitro dyestuff having a shade, on the Munsell scale from 10 Y to 2.5 Y, these violet and yellow dyestuffs being present in proportions such that their selectivity coefficients are substantially equal, the coefficients being from 3 to 8 when determined at a concentration of 0.1 to 0.6% by weight, the ratio by weight of the violet dyestuff to the yellow dyestuff being from 1:1 to 3:1, so that said violet and yellow dyestuffs complement each other.

2. A composition according to claim 1, in which the violet nitro dyestuff is a N-substituted 2-nitro-p-phenylenediamine of the formula:

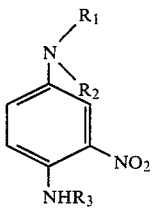

(I)

in which $R_1$ denotes the β-hydroxyethyl group, $R_2$ denotes the β-hydroxyethyl or methyl group and $R_3$ denoted the β-hydroxyethyl or methyl group, or the β-aminoethyl group if $R_2$ denotes the β-hydroxyethyl group, and the yellow nitro dyestuff is an o- or p-nitroaniline of the formula:

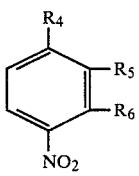

(II)

in which $R_4$ denotes hydrogen, $R_5$ denotes the isopropyl group and $R_6$ denotes the amino group; or $R_4$ denotes the β-hydroxyethoxy group, $R_5$ denotes hydrogen and $R_6$ denotes the methylamino or β-hydroxyethylamino group; or $R_4$ denotes the β,γ-dihydroxypropoxy group, $R_5$ denotes hydrogen and $R_6$ denotes the amino, methylamino or β-hydroxyethylamino group; or $R_4$ denotes the β-hydroxyethylamino group, $R_5$ denotes the methoxy group and $R_6$ denotes hydrogen; or $R_4$ denotes the methoxy group, $R_5$ denotes hydrogen and $R_6$ denotes the β-hydroxyethylamino, β-hydroxypropylamino or β,γ-dihydroxypropylamino group.

3. A composition according to claim 1, in which the violet dyestuff and the yellow dyestuff are used in a total concentration from 0.04% to 2.5% by weight.

4. A composition according to claim 1, which also comprises a tinctorially effective amount of one or more 3-nitro-aminophenols of the formula:

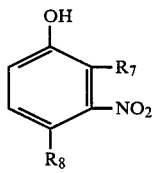

(III)

in which $R_7$ denotes hydrogen and $R_8$ denotes the amino or β-hydroxyethylamino group; or $R_7$ denotes the amino group and $R_8$ denotes hydrogen.

5. A composition according to claim 1, which also comprises a tinctorially effective amount of one or more nitro-aminobenzenes of the formula:

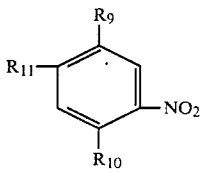

in which $R_9$ denotes the hydroxyl group, $R_{10}$ denotes hydrogen and $R_{11}$ denotes the N-($\beta$-hydroxyethyl)-amino group; or $R_9$ denotes the $\beta$-hydroxyethoxy or $\beta,\gamma$-dihydroxy-propoxy group, $R_{10}$ denotes the N-($\beta$-hydroxyethyl)-amino group and $R_{11}$ denotes hydrogen.

6. A composition according to claim 4, which contains 0.001 to 2.5% by weight of one or more dyestuffs of formula (III).

7. A composition according to claim 5 which contains 0.001 to 2.5% by weight of one or more dyestuffs of formula (IV).

8. A composition according to claim 1, which comprises, in an aqueous vehicle a solvent selected from the group consisting of ethyl alcohol, isopropyl alcohol, benzyl alcohol, glycol and glycol ether, at a concentration of 0.5 to 20% by weight.

9. A composition according to claim 8 wherein said solvent is at a concentration of 2 to 10% by weight.

10. A composition according to claim 1, which comprises an anionic, cationic, amphoteric or non-ionic surface-active agent or a mixture thereof, at a concentration of 0.05 to 50% by weight.

11. A composition according to claim 10 which comprises a said surface-active agent at a concentration of 0.5 to 10% by weight.

12. A composition according to claim 1 which comprises a fatty acid amide selected from the group consisting of mono- and diethanolamides of fatty acids of copra, lauric, or oleic acid, at a concentration of 0.05 to 10% by weight.

13. A composition according to claim 1 which comprises a thickener at a concentration of 0.5 to 15% by weight.

14. A composition according to claim 1 which has a pH of 6 to 11.

15. A composition according to claim 14 which has a pH of 8 to 10.

16. Process for dyeing human hair by direct coloration, which comprises subjecting the hair to a lightening treatment by applying, to the head of hair, an ammoniacal solution of hydrogen peroxide, a solution of hydrogen peroxide containing an alkaline agent, or an ammoniacal solution of an alkali metal peroxide or persalt, urea peroxide or an addition compound of hydrogen peroxide and an organic compound, and, simultaneously or after 5 to 30 minutes and rinsing with water, applying a composition as defined in claim 1, to the hair, leaving it on the hair 15 to 30 minutes and then rinsing and drying the hair.

17. A composition having less than twice the number of mutants as the control, as tested by the Ames test, which is suitable for the direct coloration of human hair, said composition comprising a violet dyestuff which is N-methyl, $N^4$, $N^4$-bis(beta-hydroxyethyl)-2-nitro-p-phenylenediamine and a yellow dyestuff which is 4-nitro 3-methylamino-phenoxyethanol, the composition containing 0.04 to 2.5% by weight of said dyestuffs, the ratio by weight of the violet dyestuff to the yellow dyestuff being from 1:1 to 3:1.

* * * * *